US008787608B2

(12) United States Patent
Van Himbeeck et al.

(10) Patent No.: US 8,787,608 B2
(45) Date of Patent: Jul. 22, 2014

(54) VIBRATION ISOLATION IN A BONE CONDUCTION DEVICE

(75) Inventors: Carl Van Himbeeck, Zottegem (BE); Marcus Andersson, Göteborg (SE); David N. Morris, Dover Height (AU); Gunnar Kristian Åsnes, Mölndal (SE)

(73) Assignee: Cochlear Limited, Macquarie University (AU)

( * ) Notice: Subject to any disclaimer, the term of this patent is extended or adjusted under 35 U.S.C. 154(b) by 179 days.

(21) Appl. No.: 13/114,633

(22) Filed: May 24, 2011

(65) Prior Publication Data

US 2012/0302822 A1 Nov. 29, 2012

(51) Int. Cl.
*H04R 25/00* (2006.01)
*A61N 1/00* (2006.01)

(52) U.S. Cl.
USPC ............. 381/326; 381/151; 381/380; 600/25; 607/55; 607/57

(58) Field of Classification Search
CPC ...... H04R 2460/13; H04R 11/00; H04R 1/14; H04R 25/606; H04R 2225/67; A61N 1/0541; A61F 11/04
USPC .......... 381/326, 151, 380; 600/25; 607/55, 57
See application file for complete search history.

(56) References Cited

U.S. PATENT DOCUMENTS 2,390,243 A * 12/1945 Faltico .......................... 381/326
4,498,461 A * 2/1985 Hakansson ..................... 600/25
4,997,056 A * 3/1991 Riley ............................ 181/136
5,208,867 A * 5/1993 Stites, III ...................... 381/361
7,072,476 B2 * 7/2006 White et al. .................... 381/74
7,376,237 B2 * 5/2008 Westerkull .................... 381/326
8,170,252 B2 * 5/2012 Parker et al. .................. 381/326
2006/0050913 A1 3/2006 Westerkull
2006/0161255 A1 7/2006 Zarowski et al.
2007/0053536 A1 * 3/2007 Westerkull .................... 381/326
2008/0205679 A1 * 8/2008 Darbut et al. ................. 381/328
2008/0319250 A1 * 12/2008 Asnes ............................ 600/25
2009/0245554 A1 10/2009 Parker
2009/0304209 A1 * 12/2009 Nakatani ....................... 381/151
2010/0137675 A1 * 6/2010 Parker ............................ 600/25

(Continued)

FOREIGN PATENT DOCUMENTS

| | | |
|---|---|---|
| EP | 0326905 | 8/1989 |
| KR | 10-2009-0076484 A | 7/2009 |
| WO | 02/084866 | 10/2002 |

OTHER PUBLICATIONS

International Search Report and Written Opinion for International Application No. PCT/IB2012/052625 mailed Jan. 21, 2013 (15 pages).

(Continued)

*Primary Examiner* — Duc Nguyen
*Assistant Examiner* — Sean H Nguyen
(74) *Attorney, Agent, or Firm* — Lowe Hauptman & Ham, LLP

(57) ABSTRACT

A bone conduction device, including a bone fixture adapted to be fixed to bone, a vibratory element adapted to be attached to the bone fixture and configured to vibrate in response to sound signals, and a vibration isolator adapted to be disposed between the vibratory element and the bone.

33 Claims, 10 Drawing Sheets

(56) References Cited

U.S. PATENT DOCUMENTS

| | | | | |
|---|---|---|---|---|
| 2010/0330534 | A1* | 12/2010 | Hyun | 433/174 |
| 2011/0152601 | A1 | 6/2011 | Puria et al. | |
| 2011/0268303 | A1* | 11/2011 | Ahsani | 381/326 |
| 2011/0319021 | A1* | 12/2011 | Proulx et al. | 455/41.2 |
| 2012/0088956 | A1 | 4/2012 | Asnes et al. | |
| 2012/0108887 | A1* | 5/2012 | Vermeiren | 600/25 |
| 2012/0302823 | A1 | 11/2012 | Andersson et al. | |

OTHER PUBLICATIONS

European Extended Search Report and Search Opinion for European Application No. 09753352.5 mailed Feb. 15, 2013 (7 pages).

International Search Report for PCT/IB2013/054518, published on WIPO website on Jan. 22, 2014.

* cited by examiner

VIBRATION ISOLATION IN A BONE CONDUCTION DEVICE

BACKGROUND

1. Field of the Invention

The present invention relates generally to bone conduction devices, and more particularly, to vibration isolation in a bone conduction device.

2. Related Art

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses a component positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, certain types of hearing prostheses commonly referred to as bone conduction devices, convert a received sound into mechanical vibrations. The vibrations are transferred through the skull to the cochlea causing generation of nerve impulses, which result in the perception of the received sound. Bone conduction devices may be a suitable alternative for individuals who cannot derive sufficient benefit from acoustic hearing aids, cochlear implants, etc.

SUMMARY

In accordance with one aspect of the present invention, there is a bone conduction device, comprising a bone fixture adapted to be fixed to bone, a vibratory element adapted to be attached to the bone fixture and configured to vibrate in response to sound signals, a vibration isolator adapted to be disposed between the vibratory element and the bone.

In accordance with another aspect of the present invention, there is a method of converting a percutaneous bone conduction device comprising a bone fixture implanted in a recipient's skull, and an attached abutment, the method comprising removing the abutment from the bone fixture and attaching a vibratory element to the bone fixture such that a vibration isolator is positioned between the vibratory element and the skull adjacent the bone fixture.

In accordance with another aspect of the present invention, there is an implantable component of a bone conduction device, comprising vibrational means for generating mechanical vibrations in response to received signals, attachment means for securing the vibrational means to a recipient's skull, and vibration isolation means, configured to be disposed between the vibrational means and the skull and adjacent the attachment means, and configured to substantially prevent mechanical vibrations from directly entering the skull except through the attachment means.

In accordance with another aspect of the present invention, there is a transcutaneous bone conduction device, comprising a bone fixture adapted to be fixed to bone, and a vibratory element adapted to be attached to the bone fixture and configured to generate vibrational energy in response to a sound signal, wherein substantially all of the vibrational energy transmitted to the bone is transmitted to the bone via the bone fixture.

In accordance with another aspect of the present invention, there is a method of enhancing hearing of a recipient, the method comprising, capturing a sound signal, vibrating a vibratory element in response to the captured sound signal, thereby generating vibrational energy, and conducting more of the vibrational energy from the vibratory element to bone of the recipient via an artificial pathway extending from the vibratory element to the bone than is conducted directly from the vibratory element to the bone.

BRIEF DESCRIPTION OF THE DRAWINGS

Embodiments of the present invention are described below with reference to the attached drawings, in which.

DETAILED DESCRIPTION

Aspects of the present invention are generally directed to a bone conduction device configured to deliver mechanical vibrations to a recipient's cochlea via the skull to cause a hearing percept. The implantable component of the bone conduction device includes a bone fixture adapted to be secured to the skull and a vibratory element attachable to the bone fixture. The vibratory element vibrates in response to sound received by the device. The implantable component also includes a vibration isolator configured to be disposed between the vibratory element and the skull. The vibration isolator is configured to substantially prevent vibration generated by the vibratory element from being transferred directly from the vibrator to the skull. As such, vibrations transferred to the skull are primarily transferred from the vibratory element through the bone fixture.

In certain embodiments of the present invention, the bone conduction device is a passive transcutaneous bone conduction device. In such embodiments, the vibratory element may comprise an implantable magnetic plate that vibrates in response to vibrations transmitted through the skin of the recipient generated by an external magnetic plate.

In other embodiments of the present invention, the bone conduction device is an active transcutaneous bone conduction device. In such embodiments, the vibratory element may comprise an implantable actuator configured to deliver vibrations directly to the bone fixture.

Figure 1:
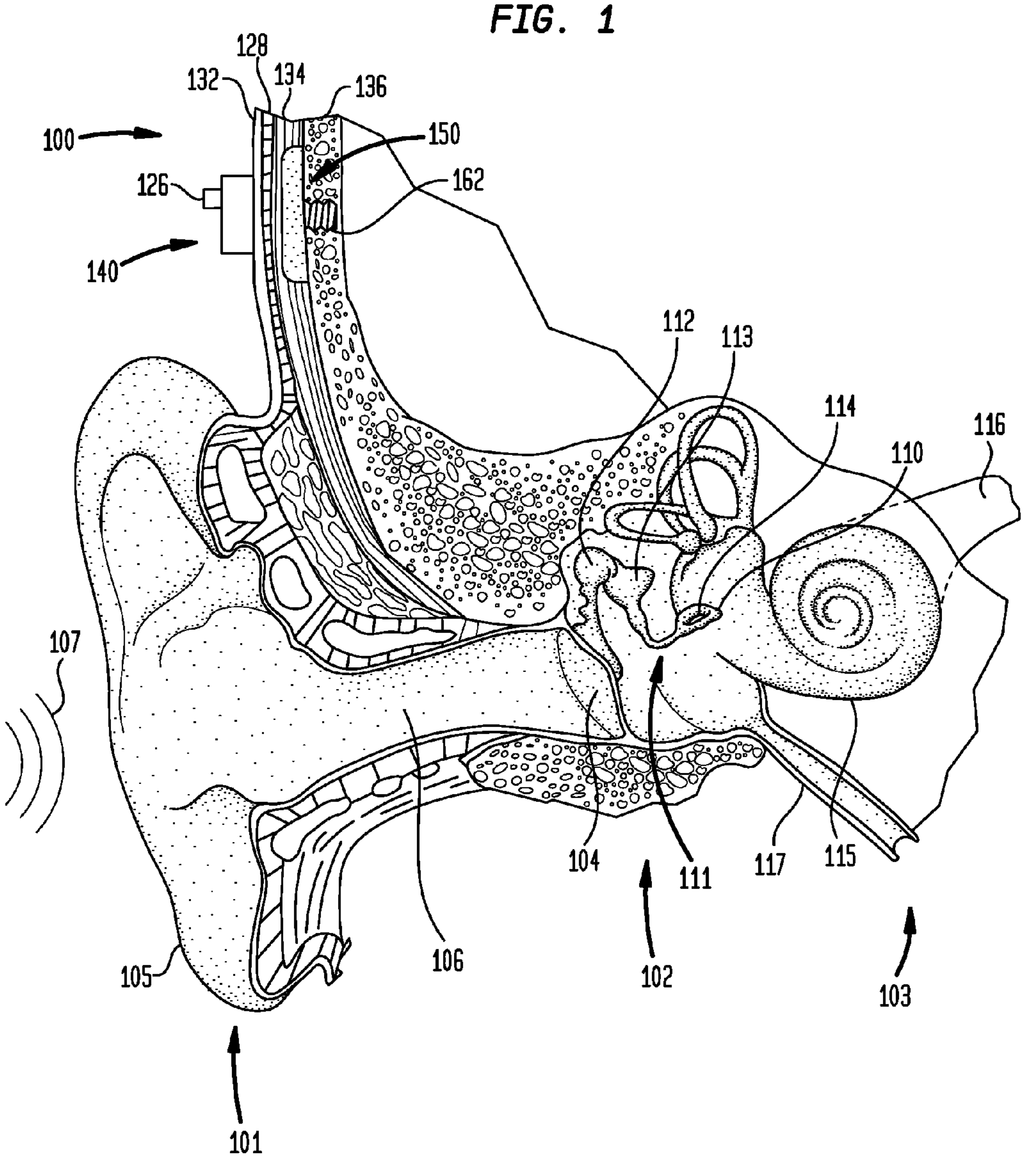
FIG. 1 is a perspective view of an exemplary bone conduction device in which embodiments of the present invention may be implemented.

FIG. 1 is a perspective view of a transcutaneous bone conduction device 100 in which embodiments of the present invention may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 110 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient. Bone conduction device 100 comprises an external component 140 and implantable component 150. The bone conduction device 100 includes a sound input element 126 to receive sound signals. Sound input element 126 may comprise, for example, a microphone, telecoil, etc. In an exemplary embodiment, sound input element 126 may be located, for example, on or in bone conduction device 100, on a cable or tube extending from bone conduction device 100, etc. Alternatively, sound input element 126 may be subcutaneously implanted in the recipient, or positioned in the recipient's ear. Sound input element 126 may also be a component that receives an electronic signal indicative of sound, such as, for example, from an external audio device. For example, sound input element 126 may receive a sound signal in the form of an electrical signal from an MP3 player electronically connected to sound input element 126.

Bone conduction device 100 comprises a sound processor (not shown), an actuator (also not shown) and/or various other operational components. In operation, sound input device 126 converts received sounds into electrical signals. These electrical signals are utilized by the sound processor to generate control signals that cause the actuator to vibrate. In other words, the actuator converts the electrical signals into mechanical vibrations for delivery to the recipient's skull.

In accordance with embodiments of the present invention, a fixation system 162 may be used to secure implantable component 150 to skull 136. As described below, fixation system 162 may be a bone screw fixed to skull 136, and also attached to implantable component 150.

In one arrangement of FIG. 1, bone conduction device 100 is a passive transcutaneous bone conduction device. That is, no active components, such as the actuator, are implanted beneath the recipient's skin 132. In such an arrangement, the active actuator is located in external component 140, and implantable component 150 includes a magnetic plate, as will be discussed in greater detail below. The magnetic plate of the implantable component 150 vibrates in response to vibration transmitted through the skin, mechanically and/or via a magnetic field, that are generated by an external magnetic plate.

In another arrangement of FIG. 1, bone conduction device 100 is an active transcutaneous bone conduction device where at least one active component, such as the actuator, is implanted beneath the recipient's skin 132 and is thus part of the implantable component 150. As described below, in such an arrangement, external component 140 may comprise a sound processor and transmitter, while implantable component 150 may comprise a signal receiver and/or various other electronic circuits/devices.

Aspects of the present invention may also include the conversion of an implanted percutaneous bone conduction device to a transcutaneous bone conduction device. To this end, an exemplary percutaneous bone conduction device will be briefly described below.

Figure 2A:
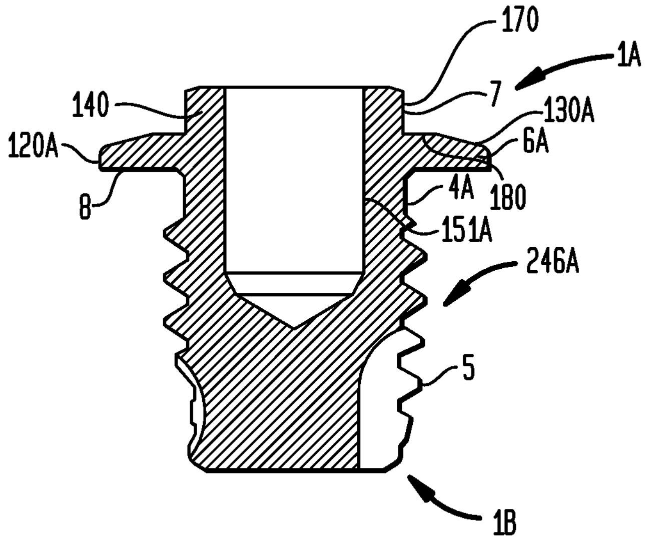
FIGS. 2A and 2B are schematic diagrams of exemplary bone fixtures with which embodiments of the present invention may be implemented.
Figure 2B:
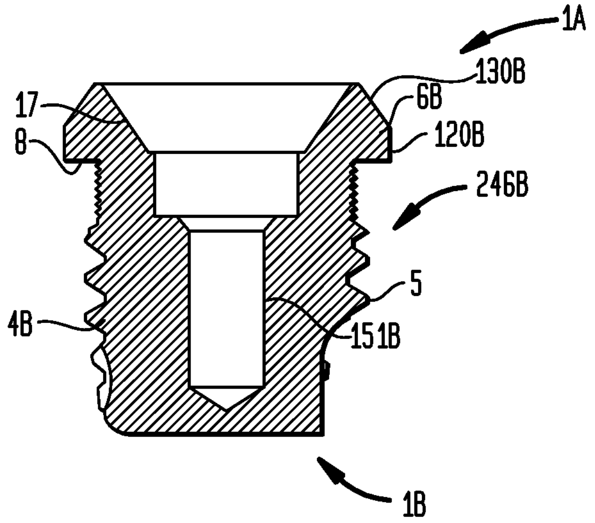

As previously noted, aspects of the present invention are generally directed to a bone conduction device including an implantable component comprising a bone fixture adapted to be secured to the skull, a vibratory element attached to the bone fixture, and a vibration isolator disposed between the vibratory element and the recipient's skull. FIGS. 2A and 2B are cross-sectional views of bone fixtures 246A and 246B that may be used in exemplary embodiments of the present invention. Bone fixtures 246A and 246B are configured to receive an abutment as is known in the art, where an abutment screw is used to attach the abutment to the bone fixtures, as will be detailed below.

Bone fixtures 246A and 246B may be made of any material that has a known ability to integrate into surrounding bone tissue (i.e., it is made of a material that exhibits acceptable osseointegration characteristics). In one embodiment, the bone fixtures 246A and 246B are made of titanium.

As shown, fixtures 246A and 246B each include main bodies 4A and 4B, respectively, and an outer screw thread 5 configured to be installed into the skull. The fixtures 246A and 246B also each respectively comprise flanges 6A and 6B configured to prevent the fixtures from being inserted too far into the skull. Fixtures 246A and 246B may further comprise a tool-engaging socket having an internal grip section for easy lifting and handling of the fixtures. Tool-engaging sockets and the internal grip sections usable in bone fixtures according to some embodiments of the present invention are described and illustrated in U.S. Provisional Application No. 60/951,163, entitled “Bone Anchor Fixture for a Medical Prosthesis,” filed Jul. 20, 2007.

Main bodies 4A and 4B have a length that is sufficient to securely anchor the bone fixtures into the skull without penetrating entirely through the skull. The length of main bodies 4A and 4B may depend, for example, on the thickness of the skull at the implantation site. In one embodiment, the main bodies of the fixtures have a length that is no greater than 5 mm, measured from the planar bottom surface 8 of the flanges 6A and 6B to the end of the distal region 1B. In another embodiment, the length of the main bodies is from about 3.0 mm to about 5.0 mm.

In the embodiment depicted in FIG. 2A, main body 4A of bone fixture 246A has a cylindrical proximate end 1A, a straight, generally cylindrical body, and a screw thread 5. The distal region 1B of bone fixture 246A may be fitted with self-tapping cutting edges formed into the exterior surface of the fixture. Further details of the self-tapping features that may be used in some embodiments of bone fixtures used in embodiments of the present invention are described in International Patent Application WO 02/09622.

Additionally, as shown in FIG. 2A, the main body of the bone fixture 246A has a tapered apical proximate end 1A, a straight, generally cylindrical body, and a screw thread 5. The distal region 1B of bone fixtures 246A and 246B may also be fitted with self-tapping cutting edges (e.g., three edges) formed into the exterior surface of the fixture.

A clearance or relief surface may be provided adjacent to the self-tapping cutting edges in accordance with the teachings of U.S. Patent Application Publication No. 2009/0082817. Such a design may reduce the squeezing effect between the fixture 246A and the bone during installation of the screw by creating more volume for the cut-off bone chips.

As illustrated in FIGS. 2A-2B, flanges 6A and 6B have a planar bottom surface for resting against the outer bone surface, when the bone fixtures have been screwed down into the skull. In an exemplary embodiment, the flanges 6A and 6B have a diameter which exceeds the peak diameter of the screw threads 5 (the screw threads 5 of the bone fixtures 246A and 246B may have an outer diameter of about 3.5-5.0 mm). In one embodiment, the diameter of the flanges 6A and 6B exceeds the peak diameter of the screw threads 5 by approximately 10-20%. Although flanges 6A and 6B are illustrated in FIGS. 2A-2B as being circumferential, the flanges may be configured in a variety of shapes. Also, the size of flanges 6A and 6B may vary depending on the particular application for which the bone conduction implant is intended.

In FIG. 2B, the outer peripheral surface of flange 6B has a cylindrical part 120B and a flared top portion 130B. The upper end of flange 6B is designed with an open cavity having a tapered inner side wall 17. The tapered inner side wall 17 is adjacent to the grip section (not shown).

It is noted that the interiors of the fixtures 246A and 246B further respectively include an inner bottom bore 151A and 151B having internal screw threads for securing a coupling shaft of an abutment screw to secure respective abutments to the respective bone fixtures as will be described in greater detail below.

In FIG. 2A, the upper end 1A of fixture 246A is designed with a cylindrical boss 140 having a coaxial outer side wall 170 extending at a right angle from a planar surface 180A at the top of flange 6A.

In the embodiments illustrated in FIGS. 2A and 2B, the flanges 6A and 6B have a smooth, open upper end and do not have a protruding hex. The smooth upper end of the flanges and the absence of any sharp corners provides for improved soft tissue adaptation. Flanges 6A and 6B also comprises a cylindrical part 120A and 120B, respectively, that together with the flared upper parts 130A and 130B, respectively, provides sufficient height in the longitudinal direction for internal connection with the respective abutments that may be attached to the bone fixtures.

Figure 3:
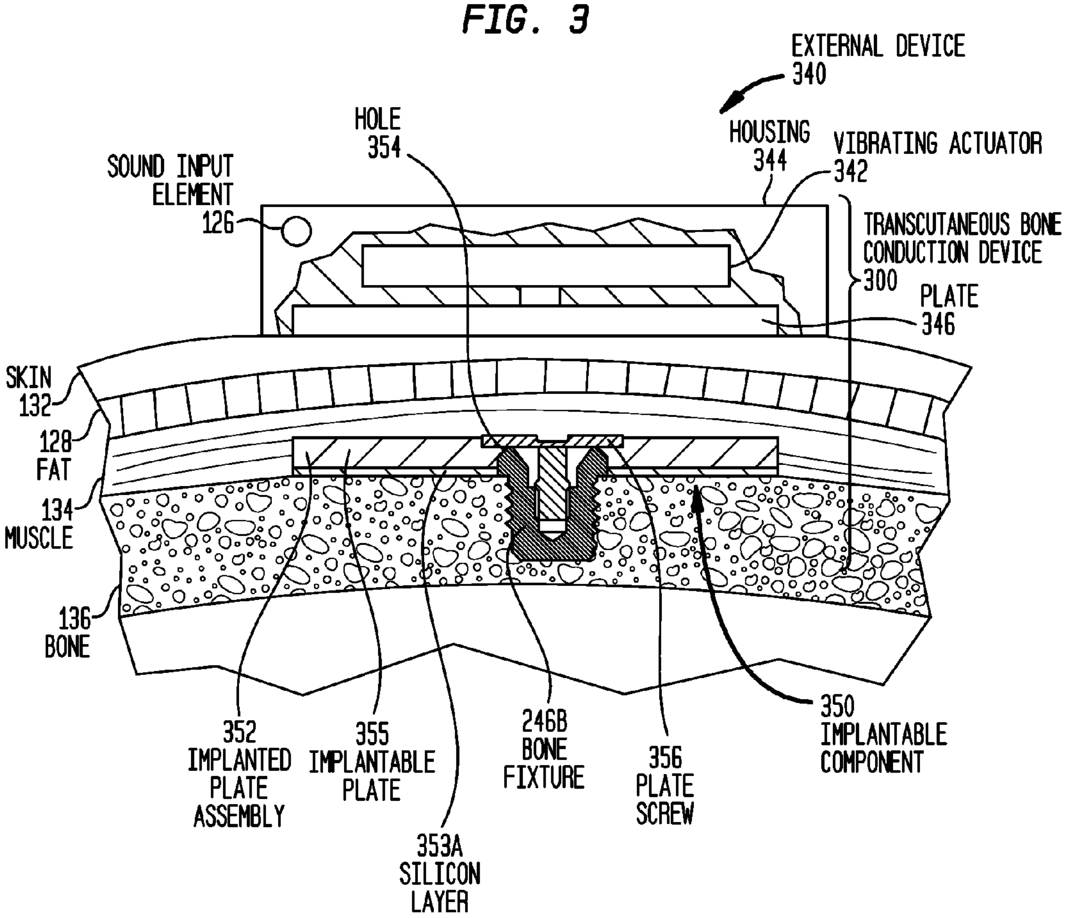
FIG. 3 is a schematic diagram illustrating an exemplary passive transcutaneous bone conduction device in which embodiments of the present invention may be implemented.

FIG. 3 depicts an exemplary embodiment of a transcutaneous bone conduction device 300 according to an embodiment of the present invention that includes an external device 340 and an implantable component 350. The transcutaneous bone conduction device 300 of FIG. 3 is a passive transcutaneous bone conduction device in that a vibrating actuator 342 is located in the external device 340. Vibrating actuator 342 is located in housing 344 of the external component, and is coupled to plate 346. Plate 346 may be in the form of a permanent magnet and/or in another form that generates and/or is reactive to a magnetic field, or otherwise permits the establishment of magnetic attraction between the external device 340 and the implantable component 350 sufficient to hold the external device 340 against the skin of the recipient.

In an exemplary embodiment, the vibrating actuator 342 is a device that converts electrical signals into vibration. In operation, sound input element 126 converts sound into electrical signals. Specifically, the transcutaneous bone conduction device 300 provides these electrical signals to vibrating actuator 342, or to a sound processor (not shown) that processes the electrical signals, and then provides those processed signals to vibrating actuator 342. The vibrating actuator 342 converts the electrical signals (processed or unprocessed) into vibrations. Because vibrating actuator 342 is mechanically coupled to plate 346, the vibrations are transferred from the vibrating actuator 342 to plate 346. Implanted plate assembly 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient. Accordingly, vibrations produced by the vibrating actuator 342 of the external device 340 are transferred from plate 346 across the skin to plate 355 of plate assembly 352. This may be accomplished as a result of mechanical conduction of the vibrations through the skin, resulting from the external device 340 being in direct contact with the skin and/or from the magnetic field between the two plates. These vibrations are transferred without penetrating the skin with a solid object such as an abutment as detailed herein with respect to a percutaneous bone conduction device.

As may be seen, the implanted plate assembly 352 is substantially rigidly attached to bone fixture 246B in this embodiment. As indicated above, bone fixture 246A or other bone fixture may be used instead of bone fixture 246B in this and other embodiments. In this regard, implantable plate assembly 352 includes through hole 354 that is contoured to the outer contours of the bone fixture 246B. This through hole 354 thus forms a bone fixture interface section that is contoured to the exposed section of the bone fixture 246B. In an exemplary embodiment, the sections are sized and dimensioned such that at least a slip fit or an interference fit exists with respect to the sections. Plate screw 356 is used to secure plate assembly 352 to bone fixture 246B. As can be seen in FIG. 3, the head of the plate screw 356 is larger than the hole through the implantable plate assembly 352, and thus the plate screw 356 positively retains the implantable plate assembly 352 to the bone fixture 246B. The portions of plate screw 356 that interface with the bone fixture 246B substantially correspond to an abutment screw detailed in greater detail below, thus permitting plate screw 356 to readily fit into an existing bone fixture used in a percutaneous bone conduction device. In an exemplary embodiment, plate screw 356 is configured so that the same tools and procedures that are used to install and/or remove an abutment screw (described below) from bone fixture 246B can be used to install and/or remove plate screw 356 from the bone fixture 246B.

Figure 4:
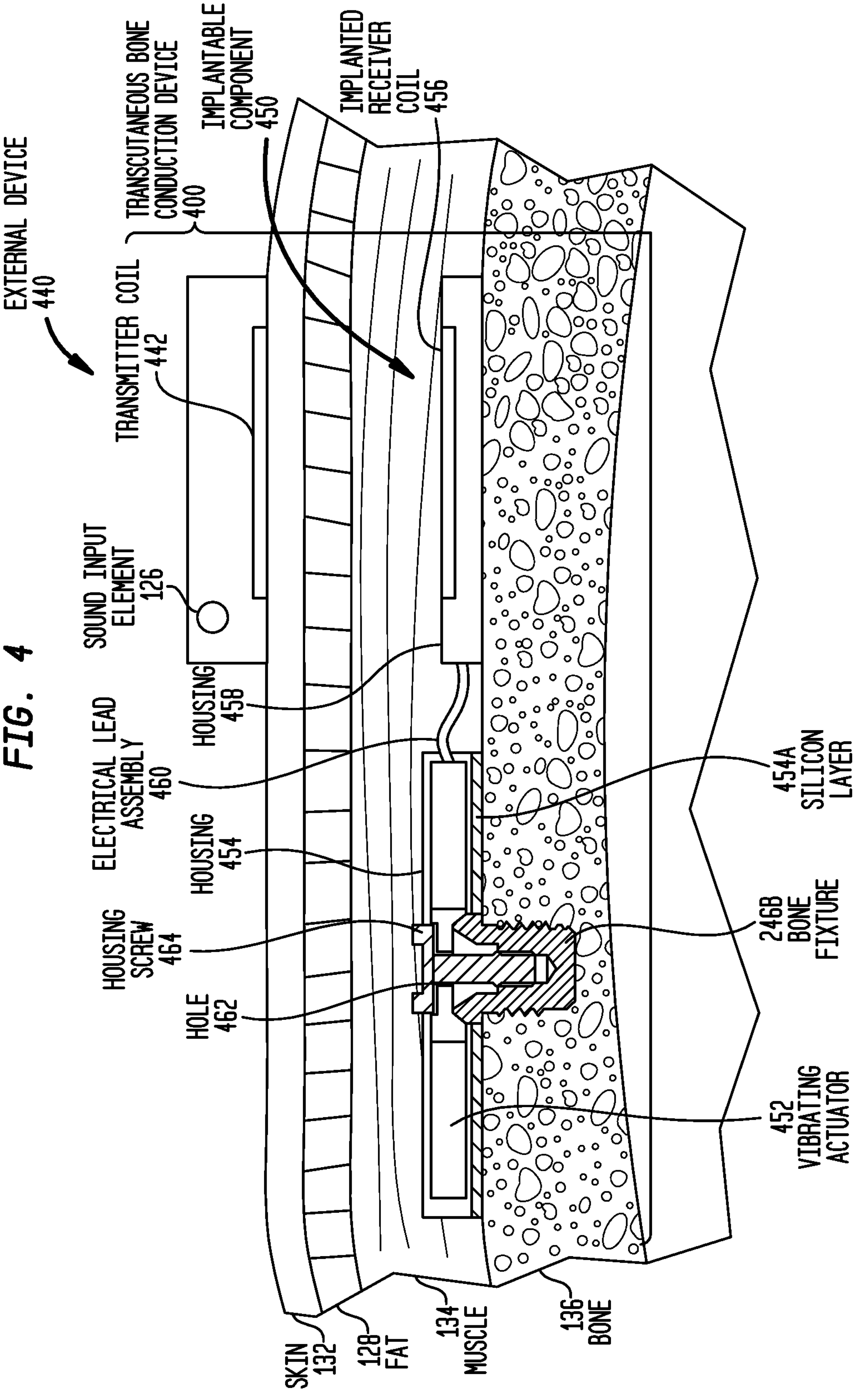
FIG. 4 is a schematic diagram illustrating an exemplary active transcutaneous bone conduction device in which embodiments of the present invention may be implemented.

FIG. 4 depicts an exemplary embodiment of a transcutaneous bone conduction device 400 according to another embodiment of the present invention that includes an external device 440 and an implantable component 450. The transcutaneous bone conduction device 400 of FIG. 4 is an active transcutaneous bone conduction device in that the vibrating actuator 452 is located in the implantable component 450. Specifically, a vibratory element in the form of vibrating actuator 452 is located in housing 454 of the implantable component 450. In an exemplary embodiment, much like the vibrating actuator 342 described above with respect to transcutaneous bone conduction device 300, the vibrating actuator 452 is a device that converts electrical signals into vibration.

External component 440 includes a sound input element 126 that converts sound into electrical signals. Specifically, the transcutaneous bone conduction device 400 provides these electrical signals to vibrating actuator 452, or to a sound processor (not shown) that processes the electrical signals, and then provides those processed signals to the implantable component 450 through the skin of the recipient via a magnetic inductance link. In this regard, a transmitter coil 442 of the external component 440 transmits these signals to implanted receiver coil 456 located in housing 458 of the implantable component 450. Components (not shown) in the housing 458, such as, for example, a signal generator or an implanted sound processor, then generate electrical signals to be delivered to vibrating actuator 452 via electrical lead assembly 460. The vibrating actuator 452 converts the electrical signals into vibrations.

The vibrating actuator 452 is mechanically coupled to the housing 454. Housing 454 and vibrating actuator 452 collectively form a vibrating element. The housing 454 is substantially rigidly attached to bone fixture 246B. In this regard, housing 454 includes through hole 462 that is contoured to the outer contours of the bone fixture 246B. Housing screw 464 is used to secure housing 454 to bone fixture 246B. The portions of housing screw 464 that interface with the bone fixture 246B substantially correspond to the abutment screw detailed below, thus permitting housing screw 464 to readily fit into an existing bone fixture used in a percutaneous bone conduction device (or an existing passive bone conduction device such as that detailed above). In an exemplary embodiment, housing screw 464 is configured so that the same tools and procedures that are used to install and/or remove an abutment screw from bone fixture 246B can be used to install and/or remove housing screw 464 from the bone fixture 246B.

More detailed features of the embodiments of FIG. 3 and FIG. 4 will now be described.

Figure 5A:
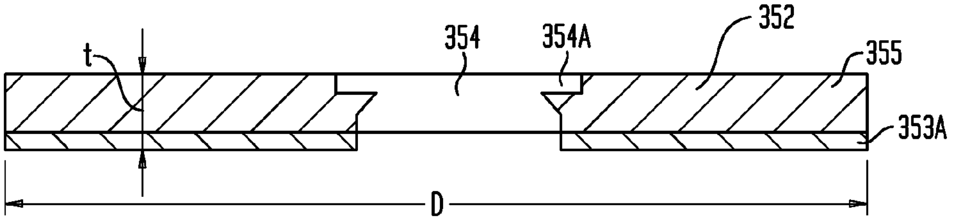
FIG. 5A is a schematic diagram illustrating an exemplary portion of the implantable component of a passive transcutaneous bone conduction device according to an embodiment of the present invention.

Referring back to FIGS. 3 and 4, the through hole 354 depicted in FIG. 3 for plate screw 354 and through hole 462 depicted in FIG. 4 for housing screw 464 may include a section that provides space for the head of the screw (e.g., 354A as illustrated in FIG. 5A). This permits the top of the respective screws to sit flush with, below or only slightly proud of the top surface of the plate 355 or housing 454, respectively. However, in other embodiments, the entire head of the plate screw 356 or housing screw 456 sits proud of the top surface of the respective plate assembly 352 and housing 454.

Figure 5B:
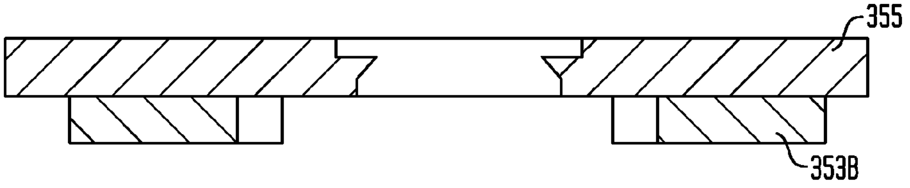
FIG. 5B is a schematic diagram illustrating another exemplary portion of the implantable component of a passive transcutaneous bone conduction device according to an embodiment of the present invention.

As noted above, implanted plate assembly 352 is substantially rigidly attached to bone fixture 246B to form the implantable component 350. The attachment formed between the implantable plate assembly 352 and the bone fixture 246B is one that inhibits the transfer of vibrations of the implantable plate assembly 352 to the bone fixture 246B as little as possible. Moreover, an embodiment of the present invention is directed towards vibrationally isolating the implantable plate assembly 352 from the skull 136 as much as possible. That is, an embodiment of the present invention is directed to an implantable component 340 that, except for a path for the vibrational energy through the bone fixture, the vibratory element is vibrationally isolated from the skull. In this regard, an embodiment of the implantable plate assembly 352 includes a silicon layer 353A or other biocompatible vibrationally isolating substance interposed between an implantable plate 355, corresponding to a vibratory element, and the skull 136, as may be seen in FIG. 5A. Thus, in the embodiment of FIG. 5A, the plate assembly 352 includes implantable plate 355 and silicon layer 352A. The silicon layer 353A corresponds to a vibration isolator and attenuates some of the vibrational energy that is not transmitted to the skull 136 through the bone fixture 246B. In some embodiments, a silicon layer 353A is in the form of a coating that covers only the bottom surface (i.e., the surface facing the skull 136) of the implantable plate 355 as shown in FIG. 5A, while in other embodiments, silicon covers the sides and/or the top of the implantable plate 355. The silicon layer is attached to the outer surface of the implantable plate 355. In some embodiments, silicon only covers portions of the bottom, sides and/or top, as is depicted by way of example in FIG. 5B, where a plurality of separate silicon pillars 353B are located on the bottom surface of the implantable plate 355. In some embodiments, the vibration isolator comprises a substantially planar ring disposed substantially around the outer surface of the bone fixture. This ring may be a single piece or may be formed by multiple sections linked together. Accordingly, an embodiment of the vibration isolator includes a plurality of projections extending from the surface of the isolator abutting the skull. Any arrangement of a vibrationally isolating substance that will permit embodiments of the present invention to be practiced may be used in some embodiments. It is noted that in most embodiments, little or no silicon is located between the implantable plate 355 and the bone fixture 246B. That is, there is direct contact between the implantable plate 355 and the bone fixture 246B. In some embodiments, this contact is in the form of a slip fit or is in the form of a slight interference fit.

Figure 5C:
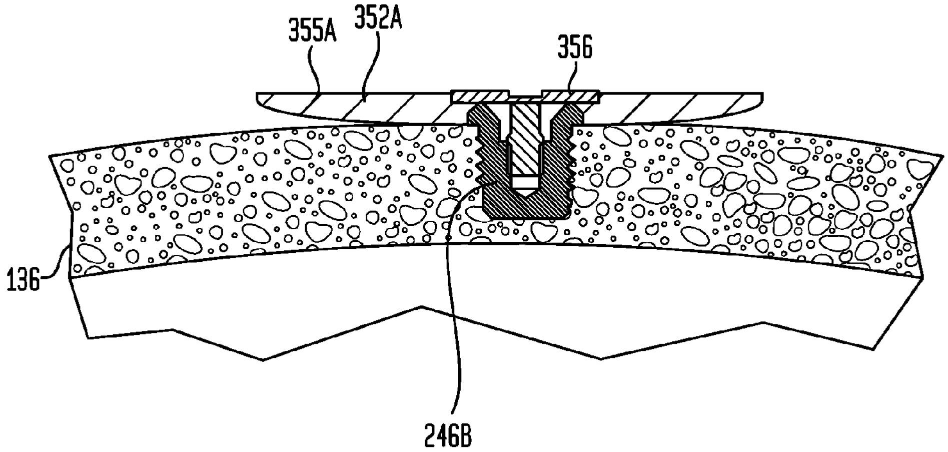
FIG. 5C is a schematic diagram illustrating another exemplary portion of the implantable component of a passive transcutaneous bone conduction device according to an embodiment of the present invention.
Figure 5D:
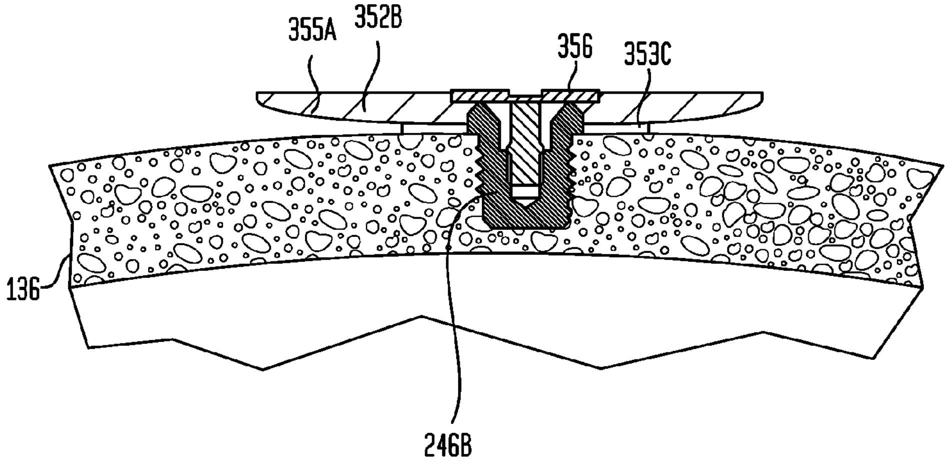
FIG. 5D is a schematic diagram illustrating another exemplary portion of the implantable component of a passive transcutaneous bone conduction device according to an embodiment of the present invention.

Moreover, in some embodiments, some or all of the implantable plate is held above the skull 136 so that there is little to no direct contact between the skull 136 and the implantable plate assembly 352. FIG. 5C depicts an exemplary implantable plate assembly 352A that includes an implantable plate 355A. In some such embodiments, tissue other than bone that is a poor conductor of vibration is encouraged to grow in the resulting space between the skull 136 and the implantable plate 355A. Also, a layer of silicon may be interposed between the implantable plate 355A and the skull 136, to further isolate the vibrations in a manner consistent with that detailed above. In this regard, FIG. 5D depicts an exemplary implantable plate assembly 352B that includes implantable plate 355A and silicon layer 353C. Silicon layer 353C may inhibit the build-up of material and/or inhibit the growth of tissue between the implantable plate 355A and the skull 136 that might otherwise create an alternate path for vibrational energy to be transmitted from the implantable plate 355A to the skull 136. As would be understood, such build-up of material/growth of tissue that provides an alternate path for vibrational energy from the implantable plate 355A might negatively affect the long-term performance of the bone conduction device. For example, continued build-up of material/growth of tissue might create, at a certain point in time after implantation, a bridge between the skull 136 and the implantable plate 355A. This might result in a relatively sudden change in the performance characteristics of the bone conduction device. Using silicon layer 353C (or other applicable vibration isolator) thus may provide an immediate improvement of the bone conduction device while also preserving that performance in the long-term. In some embodiments, the vibration isolator may include a substance that inhibits bone growth. The use of the vibration isolator to inhibit the build-up of material and/or to inhibit the growth of tissue between the vibratory element and the skull may be applicable to any of the embodiments disclosed herein and variations thereof.

In some exemplary embodiments, the vibration isolator is positioned in such a manner to reduce the risk of infection resulting from the presence of a gap between the skull 136 and the implantable plate 355. The vibration isolator may also be used to eliminate cracks and crevices that may exist in the plate 355 and/or the skull 136 that sometimes trap material therein, resulting in infections. It is to be understood that while the following description is directed to the embodiment of FIG. 3, the description is also applicable to the other embodiments disclosed herein and variations thereof. In an exemplary embodiment, the vibration isolator is configured to substantially completely fill the gap between the implantable plate 355 and the skull 136 and/or crevices therein. In some embodiments, the vibration isolator is configured to closely conform to the bone fixture 246B, such as is depicted in FIGS. 3 and 4, to reduce the risk of infection. Along these lines, the vibration isolator may have elastic properties permitting it to stretch around bone fixture 246B, thereby snugly conforming to the bone fixture 246B. The vibration isolator may include a material that is known to reduce the risk of infection and/or may be impregnated with an antibiotic. In an exemplary embodiment of the invention, the vibration isolator is a drug eluding device that eludes an antibiotic for a period of time after implantation.

In some embodiments of the present invention, the vibration isolator is configured such that once it is positioned between the skull 136 and the implantable plate assembly 352, the outer periphery of the vibration isolator extends away from the skull in a direction normal to the skull, as may be seen in FIG. 3. In some embodiments, the outer periphery extends from the skull in a substantially uniform manner, also as may be seen in FIG. 3. In other embodiments, the outer periphery of the vibration isolator extends away from the skull at an angle other than an angle normal to the surface of the skull, thereby establishing a less-abrupt transition/smoother transition that that depicted in FIG. 3. In some embodiments, the outer periphery of the vibration isolator extends away from the skull in a curved manner (e.g., semi-circular, parabolic, etc.). Any configuration that will permit the vibration isolator to smoothly extend from the skull may be used in some embodiments of the present invention.

Accordingly, the implantable component 350 is configured, in at least some embodiments, to deliver as much of the vibrational energy of implantable plate assembly 352 as possible into the skull 136 via transmission from the implantable plate assembly 352 through bone fixture 246B. Also, the implantable component 350 is configured, in at least some embodiments, to deliver as little of the vibrational energy of implantable plate assembly 352 directly into the skull 136 from the implantable plate assembly 352 as possible. An embodiment of such an implantable component 350 alleviates, at least in part, the wave propagation effect that is present as an acoustic wave propagates through a human skull, as will now be detailed.

Implantable component 350 limits the conductive channel through which vibrations enter the skull to a small area. With respect to implantable plate assembly 352, this is the area taken up by bone fixture 246B as measured on a plane tangential to the skull 136 centered at about the longitudinal axis of the bone fixture 246B. This area has a diameter that is smaller than the wavelength of the vibrations. By way of example, for vibrations having a wavelength of about 10-20 cm, the diameter of the area of the conductive channel (area taken up by bone fixture 246B) is about 3-20% of the wavelength. By comparison, if the vibrations were conducted into the skull directly from the implantable plate assembly 352, the diameter of the area of the conductive channel (area taken up by implantable plate assembly 352 as measured on a plane tangential to the skull 136 centered at about the longitudinal axis of the implantable plate assembly 352), would be a higher percentage than that of the implantable component 350 of FIG. 3, thus reducing efficiency. This is also the case with implantable plate assembly 352B, which utilizes the silicon layer 353C.

With regard to implantable plate assembly 352A, the conductive channel through which vibrations enter the skull is also limited to a small area. However, this area is the area taken up by bone fixture 246B and the portion of plate 355A that contacts skull 136, again as measured on a plane tangential to the skull 136 centered at about the longitudinal axis of the bone fixture 246B. In some embodiments, this area has a diameter that is smaller than the wavelength of the vibrations. Again by way of example, for vibrations having a wavelength of about 10-20 cm, the diameter of the area of the conductive channel (area taken up by bone fixture 246B plus the portion of plate 355A) is about 3-20% of the wavelength, notwithstanding the fact that the implantable plate assembly 352A may have an outer periphery that encompasses an area that is larger than this. That is, the implantable plate assembly 352A has a maximum outer periphery that has a corresponding maximum outer peripheral diameter, and with respect to the embodiment of FIG. 5C, where plate 355A is a circular disk, the outer periphery is the outer diameter of the disk. The implantable plate assembly 352A also includes a maximum bone contact surface area having a maximum contact surface diameter. This is the surface area of the plate 355A that directly contacts the skull 136. That is, the plate 355A only contacts the skull 136 at the maximum bone contact surface area. With respect to the embodiment of FIG. 5C, the maximum contact surface diameter is equal to or less than about half of the maximum outer peripheral diameter of the implantable plate assembly 352A. In some embodiments, the maximum outer peripheral diameter of the implantable plate assembly 352A is equal to or less than about a quarter of the maximum outer peripheral diameter of the implantable plate assembly 352A.

Accordingly, an embodiment of the present invention includes an implantable component 350 as described above configured to deliver more, substantially more and/or substantially all of the vibrational energy from an implanted vibratory element to the skull through the bone fixture 246B than directly from the implanted vibratory element to the skull.

As detailed above, the implantable plate assembly 352 may also be used to magnetically hold the external component 340 to the recipient, either as a result of the implantable plate assembly 352 comprising a permanent magnet or as a result of the implantable plate assembly 352 comprising a ferromagnetic material that reacts to a magnetic field (such as, for example, that generated by a permanent magnet located in the external component 340). Accordingly, some embodiments of the implantable plate assembly 352 should include a sufficient amount of the ferromagnetic material (and/or a sufficient area facing the external component 340) to magnetically hold the external component 340 to the recipient. In an exemplary embodiment, referring to FIG. 5A, the implantable plate assembly 352 is substantially circular, having an outer diameter of about 40 mm and having a thickness of about 4-5 mm, of which about 0.5 to 1.0 mm is silicon on the bottom and/or on the top. Also, in some embodiments, the implantable plate assembly 352 may be strengthened with ribs, either formed as an integral part of implantable plate 355 or in the form of a composite plate assembly. In other embodiments, the implantable plate assembly 352 is oval or substantially rectangular in shape (square or a rectangle having a length greater than a width). It is noted that in other embodiments of the present invention, the external device 340 or external device 440 is held in place via a means other than a magnetic field. By way of example, the external devices may be held in place via a harness such as a band that extends about the head of the recipient. In some such embodiments, the implanted plates may or may not be made of a magnetic material. In some embodiments of the passive bone conduction devices, the implanted plates may be any plate that vibrates as a result of the mechanical conduction of the vibrations from the external device to the implanted plate.

With respect to the embodiment of FIG. 4, as noted above, housing 454 is substantially rigidly attached to bone fixture 246B. The attachment formed between the housing 454 and the bone fixture 246B is one that inhibits the transfer of vibrations from the vibrating actuator 452 through the housing 454 to the bone fixture 246B as little as possible. Moreover, an embodiment of the present invention is directed towards vibrationally isolating the housing 454 from the skull 136 as much as possible, as is the case with the implantable plate assembly 352 detailed above. In this regard, an embodiment of the housing 454 includes a silicon layer 454A or other biocompatible vibrationally isolating substance interposed between the housing 454 and the skull 136. In some embodiments, a silicon layer 454A covers only the bottom surface (i.e., the surface facing the skull 136) of the housing 454 as shown in FIG. 4, while in other embodiments, silicon covers the sides and/or the top of the housing 454. In some embodiments, silicon only covers portions of the bottom, sides and/or top, in a manner analogous to that described above with respect to the implantable plate assembly 352. Any arrangement of a vibrationally isolating substance that will permit embodiments of the present invention to be practiced may be used in some embodiments.

It is noted that in most embodiments, little or no silicon is located between the housing 454 and the bone fixture 246B. That is, there is direct contact between the housing 454 and the bone fixture 246B. In some embodiments, this contact is in the form of a slip fit or is in the form of a slight interference fit. Further, it is noted that in some embodiments, the vibrating actuator 452 is mechanically coupled to the housing in such a manner as to increase the vibrational energy transferred from the vibrating actuator 452 to the bone fixture 246B as much as possible. In an exemplary embodiment, the vibrating actuator 452 is coupled to the walls of the hole 462 in a manner that enhances vibrational transfer through the walls and/or is vibrationally isolated from other portions of the housing 452 in a manner that inhibits vibrational transfer through those other portions of the housing 452.

Moreover, in some embodiments, some or all of the housing 452 is held above the skull 136 so that there is less or no direct contact between the skull 136 and the housing 452. In this regard, embodiments of the housing 452 may take an outer form corresponding to that detailed above with respect to implantable plate assembly 352A.

Accordingly, as with the implantable plate assembly 352 described above, the housing 452 is configured, in at least some embodiments, to channel as much of the vibrational energy of the vibrating actuator 452 as possible into the skull 136 via transmission from the housing 454 through bone fixture 246B. Also, as with the implantable component 350 described above, the housing 454 is configured, in at least some embodiments, to channel as little of the vibrational energy of the vibrating actuator 452 directly into the skull 136 from the housing 454 as possible. An embodiment of such housing 454 alleviates, at least in part, the wave propagation effect that is present as an acoustic wave propagates through a human skull detailed above.

It is noted that in some embodiments, housing 454 is not present and/or is not directly connected to bone fixture 246B as depicted in FIG. 4. Instead, a vibrating actuator is directly attached to the bone fixture 246B, and any components that need be shielded from body fluids are contained in a separate housing and/or the vibrating actuator does not include components that need shielding. In an exemplary embodiment, such a vibrating actuator may be a piezoelectric actuator.

In view of the various bone conduction devices detailed above, embodiments of the present invention include methods of enhancing hearing by delivering vibrational energy to a skull via an implantable component such as implantable components 300 and 400 detailed above. In an exemplary embodiment, as a first step the method comprises capturing sound with, for example, sound capture device 126 detailed above. In a second step, the captured sound signals are converted to electrical signals. In a third step, the electrical signals are outputted to a vibrating actuator configured to vibrate a vibratory element. Such a vibrating actuator may be, for example, vibrating actuator 342 of FIG. 3 configured to vibrate implantable plate assembly 352, or vibrating actuator 452, which is implanted in a recipient and where the vibratory element is part of the vibrating actuator 452. In a subsequent step, a majority of the vibrational energy from the vibrating device is conducted to the skull via an artificial pathway comprising implanted structural components extending from the vibrational device to and into the skull, thereby enhancing hearing.

In an exemplary embodiment, the artificial pathway includes any of the bone fixtures detailed herein. As may be seen in FIG. 3 and as detailed above, where the vibrating device is the implanted plate assembly 352, the artificial pathway of this method includes a section having a maximum outer diameter when measured on a first plane tangential to and on the surface of the skull at the location where the artificial pathway extends to and into the skull, of about 1% to about 20% of the wavelength of the vibrations producing the vibrational energy. In an exemplary embodiment, this diameter may correspond to the outer diameter of the bone fixture where the bone fixture enters the skull. Moreover, in an embodiment of this method, the implanted plate assembly 352 has a maximum outer diameter when measured on a second plane substantially parallel to the first plane, where the maximum outer diameter of the artificial pathway is about 5% to about 35% of the maximum outer diameter of the implanted plate assembly 352. The act of conducting a majority of the vibrational energy from the vibrating device to the skull via the artificial pathway, as opposed to, for example, directly conducting the vibrational energy from the implanted plate assembly 352 to the skull, is achieved by vibrationally isolating the implanted plate assembly 352 from the skull and rigidly coupling the implanted plate assembly 352 to the bone fixture 246B as detailed above.

It is noted that in some embodiments of this method, substantially more of the vibrational energy from the implanted plate assembly is conducted to the skull through the artificial pathway than is conducted to the skull outside of the artificial pathway. In yet other embodiments, substantially all of the vibrational energy from the implanted plate assembly is conducted to the skull through the artificial pathway.

In some embodiments, the silicon layers detailed herein inhibit osseointegration of the implantable plate 355 and the housing 454 to the skull. This permits the implantable plate 355 and/or housing 454 to be more easily removed from the recipient. Such removal may be done in the event that the implantable plate 355 and/or the housing 454 are damaged and a replacement is necessary, or simply an upgrade to those components is desired. Also, such removal may be done in the event that the recipient is in need of magnetic resonance imaging (MRI) of his or her head. Still further, if it is found that the transcutaneous bone conduction devices are insufficient for the recipient, the respective implantable plate 355 and/or the housing may be removed and an abutment may be attached to the bone fixture 246B in its place, thereby permitting conversion to a percutaneous bone conduction system. In summary, the interposition of the silicon layer between the implanted component and the skull reduces osseointegration, thus rendering removal of those components easier.

Also, the reduction in osseointegration resulting from the silicon layer may also add to the cumulative vibrational isolation of the implantable plate 355 and/or housing 454 because the components are not as firmly attached to the skull as they would otherwise be in the absence of the osseointegration inhibiting properties of the silicon layer. That is, osseointegration of the implantable plate 355 and/or housing 454 to the skull 136 may result in a coupling between the respective components and the skull 136 through which increased amounts of vibrational energy may travel directly to the skull 136 therethrough. This increased amount is relative to the amount that would travel from the respective components to the skull 136 in the absence of osseointegration. Further along these lines, some embodiments of the present invention include controlling the surface roughness of the implantable plate 355 and/or the housing 454 of the surfaces that might contact the skull 136. This is pertinent, for example, to embodiments that do not utilize a vibration isolator. In such embodiments, there may be direct contact between the vibratory element and the skull, such as, for example, embodiments consistent with that of FIG. 5C, and other embodiments where the vibratory element is raised above the skull, but the absence of the vibration isolator may permit bone tissue to grow between the vibratory element and the skull, thereby providing an alternate path for the vibration energy as detailed above. Such embodiments include implantable plate assemblies that are absent the vibration isolator (e.g., the implantable plate assembly 352 without silicon layer 353A) and housings that are absent the vibration isolator (e.g., the housing 452 without silicon layer 454A).

By way of example, the surface roughness of the bottom surface of implantable plate 355 and/or housing 452 may be polished, after the initial fabrication of the respective components, to have a surface roughness that is less conducive to osseointegration than is the case for other surface roughness values. For example, a surface roughness Ra value of less than 0.8 micrometers, such as about 0.4 micrometers or less, about 0.3 micrometers or less, about 2.5 micrometers or less and/or about 2 micrometers or less may be used for some portions of a surface or an entire surface of the implantable plate 355 that may come into contact with skull 136. This should reduce the amount of osseointegration and thus the amount of vibrational energy that is directed transferred from the implantable plate 355 to the skull 136 at the areas where the plate 355 contacts the skull 136.

Also, a reduction in osseointegration/the absence of osseointegration between the implantable plate 355 and/or the housing 454 may improve the likelihood that soft tissue and/or tissue that is less conducive to the transfer of vibrational energy than bone may grow between the respective components and the skull 136. This non-bone tissue may act as a vibration isolator having some or all of the performance characteristics of the other vibration isolators detailed herein. Additionally, the reduction in osseointegration/the absence of osseointegration between the implantable plate 355 and/or the housing 454 may likewise permit these components to be more easily removed from the recipient, such as in the case of an MRI scan of the recipient as detailed above.

In an exemplary embodiment, at least some of the surface roughness detailed above may be achieved through the use of electropolishing and/or by paste polishing. These polishing techniques may be used, for example, to reduce the surface roughness Ra of a titanium component to at least about 0.3 micrometers and 0.2 micrometers, respectively. Other methods of polishing a surface to achieve the desired surface roughnesses may be utilized in some embodiments of the present invention.

Some embodiments may include an implantable plate assembly 352 that includes both a ferromagnetic plate and a titanium component. In such an embodiment, the titanium component may be located between the ferromagnetic plate and the skull when the implantable plate assembly is fixed to the skull. For example, element 353A of FIG. 3, element 454A of FIG. 4 and/or element 353C of FIG. 5D may be made from titanium instead of silicon. The titanium component of these alternate embodiments may be polished to have one or more of the above surface roughnesses to inhibit osseointegration as detailed above.

As mentioned above, embodiments of the present invention may be implemented by converting a percutaneous bone conduction device to a transcutaneous bone conduction device. The following presents an exemplary embodiment of the present invention directed towards a method of converting a bone fixture system configured for use with a percutaneous bone conduction device to a bone fixture system configured for use with a transcutaneous bone conduction device.

In an exemplary embodiment, a surgeon or other trained professional including and not including certified medical doctors (hereinafter collectively generally referred to as a physicians) is presented with a recipient that has been fitted with a percutaneous bone conduction device, where the bone fixture system utilizes bone fixture 246B to which an abutment is connected via an abutment screw as is know in the art. More specifically, referring to FIG. 6, at step 610, the physician obtains access to a bone fixture of a percutaneous bone conduction device implanted in a skull, wherein an abutment is connected to the bone fixture 246B and extends through the skin of the recipient. At step 620, the physician removes the abutment from the bone fixture 246B. In the scenario where the abutment is attached to the bone fixture 246B via an abutment screw that extends through the abutment and is screwed into the bone fixture, this step further includes unscrewing the abutment screw from the bone fixture to remove the abutment from the bone fixture. At step 630, a vibratory element, such as the implanted plate assembly 352 in the case of a passive transcutaneous bone conduction device, is positioned beneath the skin of the recipient. In an exemplary embodiment, the vibratory element is slip fitted or interference fitted onto the bone fixture 246B, and screw 354 is screwed into the bone fixture to secure the vibratory element to the bone fixture, thereby at least one of maintaining or establishing the rigid attachment of the vibratory element to the bone fixture. It is noted that in some embodiments, the vibratory element includes a silicon layer already attached thereto. Thus, the method may effectively end at step 630. In other embodiments, the silicon layer is added later. Accordingly, an embodiment includes an optional later step, step 640, which entails positioning a vibration isolator between the vibratory element and the skull adjacent the bone fixture. In other embodiments, step 640 is performed before step 630 (the vibration isolator is first positioned on the skull and then the vibratory element is positioned on the vibration isolator).

Figure 7:
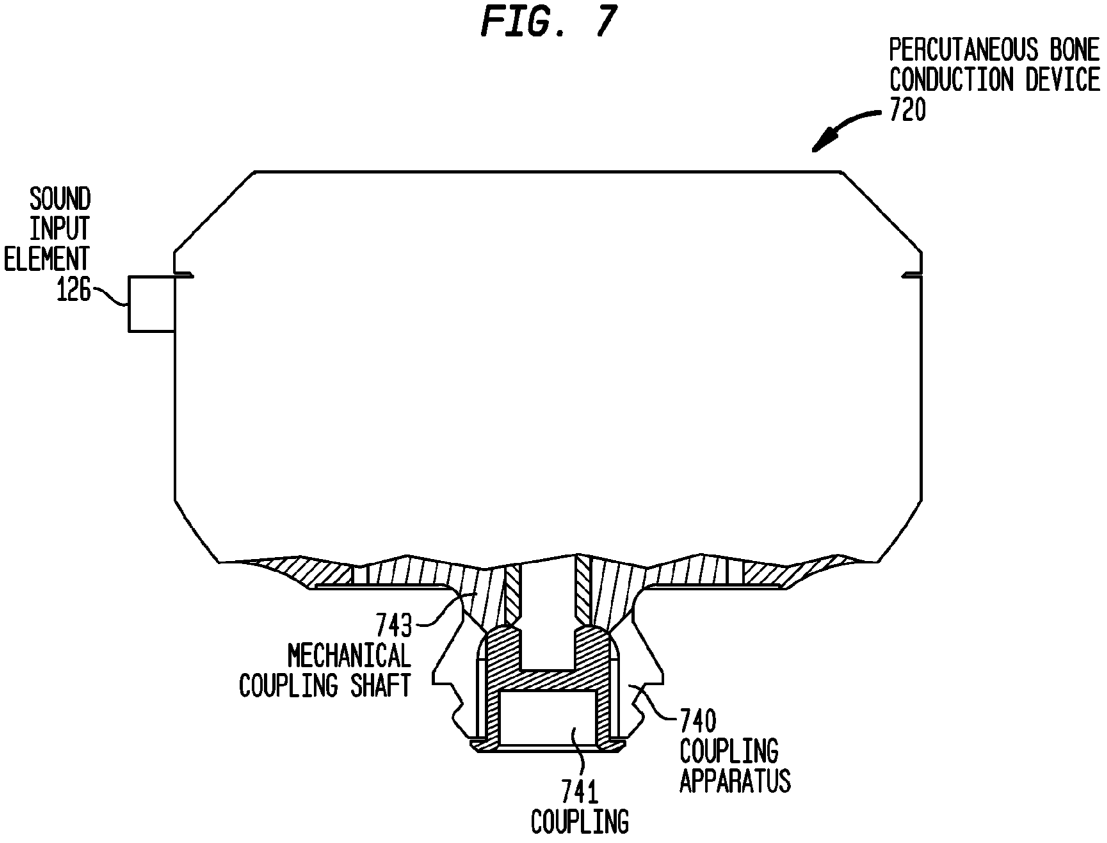
FIG. 7 is a schematic diagram illustrating a percutaneous bone conduction device with which an embodiment of the present invention may be used.

Another exemplary embodiment of the present invention includes a method of converting a percutaneous bone conduction device such as percutaneous bone conduction device 720 used in a percutaneous bone conduction device to an external device 140 for use in a passive transcutaneous bone conduction device. The percutaneous bone conduction device 720 of FIG. 7 includes a coupling apparatus 740 configured to attach the bone conduction device 720 to an abutment connected to a bone fixture implanted in the recipient. The abutment extends from the bone fixture through muscle 134, fat 128 and skin 132 so that coupling apparatus 740 may be attached thereto. Such a percutaneous abutment provides an attachment location for coupling apparatus 740 that facilitates efficient transmission of mechanical force from the bone conduction device 700. A screw holds the abutment to the bone fixture. As illustrated, the coupling apparatus 740 includes a coupling 741 in the form of a snap coupling configured to "snap couple" to a bone fixture system on the recipient.

In an embodiment, the coupling 741 corresponds to the coupling described in U.S. patent application Ser. No. 12/177,091 assigned to Cochlear Limited. In an alternate embodiment, a snap coupling such as that described in U.S. patent application Ser. No. 12/167,796 assigned to Cochlear Limited is used instead of coupling 741. In yet a further alternate embodiment, a magnetic coupling such as that described in U.S. patent application Ser. No. 12/167,851 assigned Cochlear Limited is used instead of or in addition to coupling 241 or the snap coupling of U.S. patent application Ser. No. 12/167,796.

The coupling apparatus 740 is mechanically coupled, via mechanical coupling shaft 743, to a vibrating actuator (not shown) within the bone conduction device 720. In an exemplary embodiment, the vibrating actuator is a device that converts electrical signals into vibration. In operation, sound input element 126 converts sound into electrical signals. Specifically, the bone conduction device provides these electrical signals to the vibrating actuator, or to a sound processor that processes the electrical signals, and then provides those processed signals to vibrating actuator. The vibrating actuator converts the electrical signals (processed or unprocessed) into vibrations. Because vibrating actuator is mechanically coupled to coupling apparatus 740, the vibrations are transferred from the vibrating actuator to the coupling apparatus 740 and then to the recipient via the bone fixture system (not shown).

Figure 6:
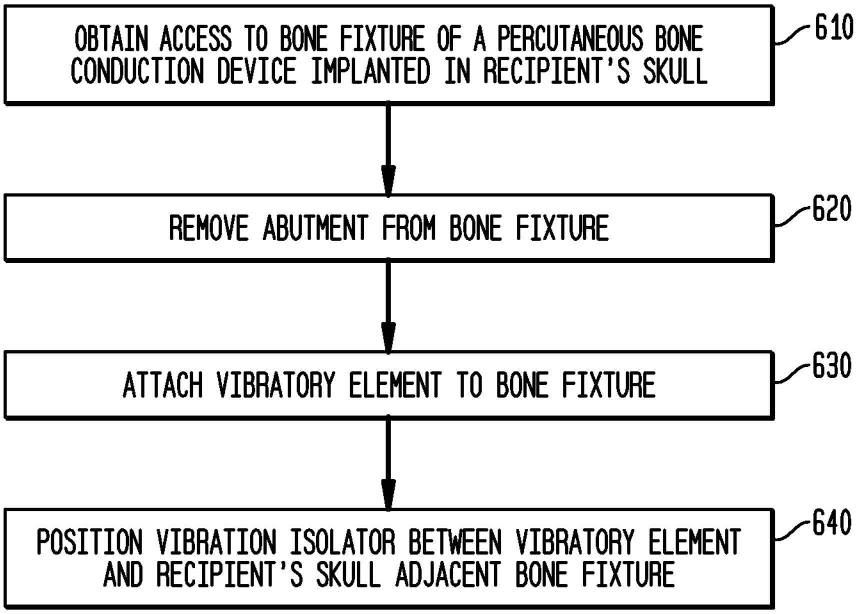
FIG. 6 depicts a flow chart detailing a method of converting a percutaneous bone conduction device to a transcutaneous bone conduction device according to an embodiment of the present invention.
Figure 8:
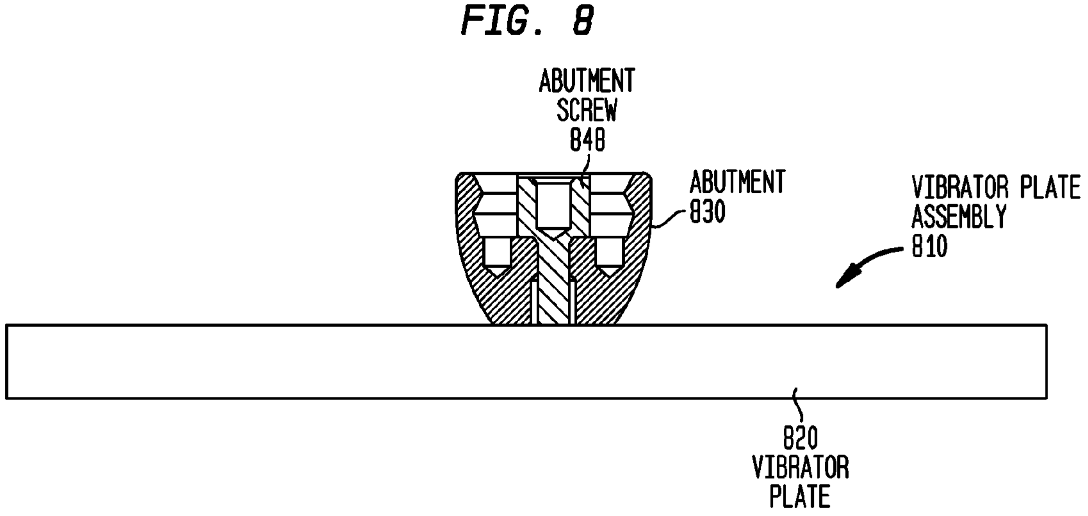
FIG. 8 is a schematic diagram illustrating an exemplary portion of the external device of a passive transcutaneous bone conduction device according to an embodiment of the present invention.
Figure 9:
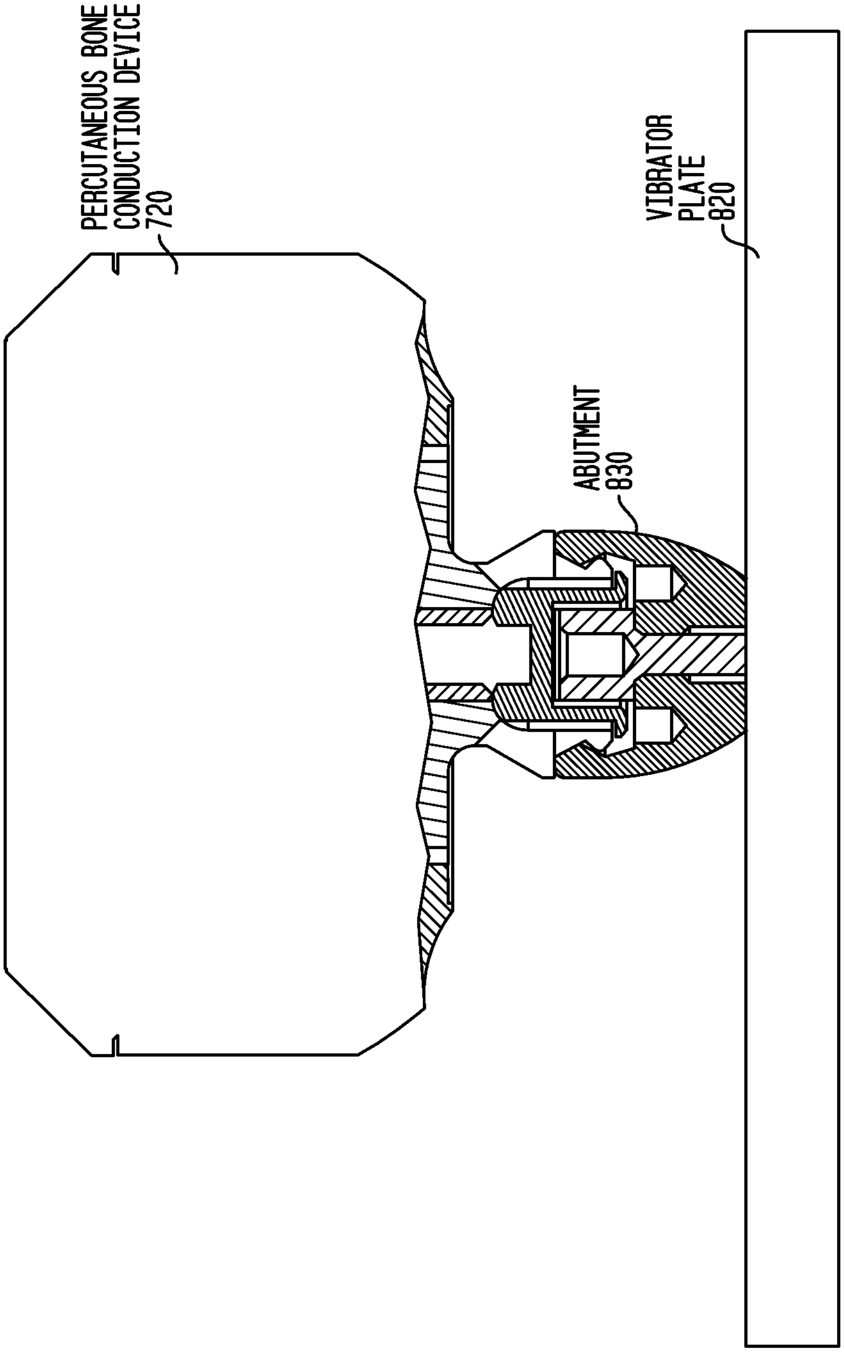
FIG. 9 is a schematic diagram illustrating an exemplary external device of a passive transcutaneous bone conduction device according to an embodiment of the present invention.

Once the abutment is removed from the bone fixture 246A or 246B (pursuant to, for example, the method detailed above with respect to FIG. 6), there is no abutment to which the coupling 741 of the percutaneous bone conduction device 720 can couple. However, an embodiment of the present invention includes a vibrator plate assembly 810 as seen in FIG. 8 that when coupled to the percutaneous bone conduction device 720 results in an external device that corresponds to an external device of a passive transcutaneous bone conduction device, as may be seen in FIG. 9.

Specifically, vibrator plate 820 of vibratory plate assembly 810 functionally corresponds to plate 346 detailed above with respect to FIG. 3, and percutaneous bone conduction device 720 functionally corresponds to vibrating actuator 342 detailed above with respect to FIG. 3. An abutment 830 is attached to vibrator plate 820 via abutment screw 848, as may be seen in FIG. 8. In an exemplary embodiment, abutment 830 is an abutment configured to connect to bone fixture 246A and/or 246B as detailed above. In alternate embodiments, abutment 830 is attached to vibrator plate 820 by other means such as, for example, welding, etc., or is integral with the vibrator plate 820. Any system that will permit vibrations from the percutaneous bone conduction device 720 to be transmitted to the vibrator plate 820 may be used with some embodiments of the present invention. As may be seen in FIG. 9, the abutment 830 permits the percutaneous bone conduction device 720 to be rigidly attached to the vibrator plate assembly 810 in a manner the same as or substantially the same as the percutaneous bone conduction device 720 is attached to a bone fixture system. Thus, the existing percutaneous bone conduction device 820 can be reused in an external device of a transcutaneous bone conduction device.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A bone conduction device, comprising:

a bone fixture adapted to be fixed to bone;

a vibratory element adapted to be attached to the bone fixture and configured to vibrate in response to a sound signal, thereby producing vibrational energy; and a vibration isolator adapted to be disposed between the vibratory element and the bone, wherein the bone fixture has a maximum outer diameter, when measured on a first plane tangential to and on the surface of the bone at a location where the bone fixture extends into the bone, of about 1% to about 20% of the wavelength of the vibrations producing the vibrational energy.

2. The bone conduction device of claim 1, wherein the vibratory element comprises:

an implantable plate configured to vibrate in response to vibrations generated by an external plate.

3. The bone conduction device of claim 2, wherein:

the implantable plate comprises a magnetic plate; and the external plate comprises a magnetic plate.

4. The bone conduction device of claim 1, wherein the vibratory element comprises an actuator configured to generate mechanical vibrations in response to delivery of electrical signals thereto.

5. The bone conduction device of claim 4, wherein the actuator is an electromagnetic actuator.

6. The bone conduction device of claim 4, wherein the actuator is a piezoelectric actuator.

7. The bone conduction device of claim 1, wherein the vibration isolator comprises a substantially planar ring disposed substantially around the outer surface of the bone fixture.

8. The bone conduction device of claim 7, wherein the vibration isolator comprises a plurality of projections extending from the surface of the isolator abutting the skull.

9. The bone conduction device of claim 1, wherein the vibration isolator is a coating on the surface of the vibratory element adjacent the skull.

10. The bone conduction device of claim 1, wherein the vibration isolator is a layer attached to the surface of the vibratory element adjacent the skull.

11. The bone conduction device of claim 1, wherein the vibration isolator is a silicon body.

12. The bone conduction device of claim 1, wherein the bone fixture comprises a bone screw having a threaded portion and screw head, and wherein the vibration isolator has a contoured recess configured to receive the screw head therein.

13. The bone conduction device of claim 3, wherein at least one of the implantable plate or the external plate comprises a permanent magnet.

14. The bone conduction device of claim 1, wherein the bone conduction device is adapted for the bone fixture to extend from the vibratory element, past the vibration isolator, and into the bone.

15. The bone conduction device of claim 1, wherein the bone conduction device is adapted for the bone fixture to extend from the vibratory element, through the vibration isolator, and into the bone.

16. The bone conduction device of claim 1, wherein the bone fixture and vibratory element are adapted to be rigidly attached, and wherein the bone conduction device is configured to substantially vibrationally isolate the vibratory element from the bone, except for a vibrational energy path through the bone fixture.

17. The bone conduction device of claim 1, wherein the vibratory element is larger than the bone fixture, and wherein the bone conduction device is configured to substantially limit a vibrational conductive channel from the vibratory element to the bone to a channel passing through the bone fixture.

18. A transcutaneous bone conduction device, comprising:

a bone fixture adapted to be fixed to bone; and a vibratory element that is larger than the bone fixture and adapted to be rigidly attached to the bone fixture and configured to generate vibrational energy in response to a sound signal, wherein substantially all of the vibrational energy transmitted to the bone is transmitted to the bone via the bone fixture, and the bone fixture has a maximum outer diameter, when measured on a first plane tangential to and on the surface of the bone at a location where the bone fixture extends into the bone, of about 1% to about 20% of the wavelength of the vibrations producing the vibrational energy.

19. The bone conduction device of claim 18, further comprising a vibration isolator adapted to be disposed between the vibratory element and the bone.

20. The bone conduction device of claim 19, wherein the vibration isolator is a silicon body.

21. The bone conduction device of claim 18, wherein:

the vibratory element includes:

a maximum outer periphery having a maximum outer peripheral diameter; and a maximum bone contact surface area having a maximum contact surface diameter;

the vibratory element is configured to contact the bone only at the maximum bone contact surface area; and the maximum contact surface diameter is substantially less than the maximum outer peripheral diameter.

22. The bone conduction device of claim 21, wherein:

the maximum contact surface diameter is less than or equal to about half of the maximum outer peripheral diameter.

23. The bone conduction device of claim 21, wherein:

the maximum contact surface diameter is less than or equal to about a quarter of the maximum outer peripheral diameter.

24. The bone conduction device of claim 18, further comprising a vibration isolator adapted to be disposed between and against the vibratory element and the bone, wherein the vibration isolator has an outer periphery that is contoured to smoothly extend away from the surface of the bone when the vibration isolator is positioned against the surface of the bone.

25. The bone conduction device of claim 18, wherein the vibratory element includes:

a surface configured to contact the bone, wherein the surface has a surface roughness Ra of about 0.4 micrometers or less.

26. The bone conduction device of claim 18, wherein the vibratory element includes:

a surface configured to contact the bone, wherein the surface has a surface roughness Ra of about 0.3 micrometers or less.

27. The bone conduction device of claim 19, wherein the bone conduction device is adapted for the bone fixture to extend from the vibratory element, past the vibration isolator, and into the bone.

28. The bone conduction device of claim 19, wherein the bone conduction device is adapted for the bone fixture to extend from the vibratory element, through the vibration isolator, and into the bone.

29. A method of enhancing hearing of a recipient, the method comprising:

capturing a sound signal;

vibrating a vibratory element in response to the captured sound signal, thereby generating vibrational energy; and conducting more of the vibrational energy from the vibratory element to bone of the recipient via an at least partially artificial pathway extending from the vibratory element to the bone than is otherwise conducted from the vibratory element to the bone, wherein an artificial portion of the at least partially artificial pathway has a maximum outer diameter, when measured on a first plane tangential to and on the surface of the bone at a location where the artificial portion of the artificial pathway contacts the bone, of about 1% to about 20% of the wavelength of the vibrations generational the vibrational energy.

30. The method of claim 29, wherein:

substantially more of the vibrational energy from the vibratory element is conducted to the bone through the at least partially artificial pathway than is otherwise conducted to the bone from the vibratory element to the bone.

31. The method of claim 29, wherein:

substantially all of the vibrational energy from the vibratory element is conducted to the bone through the at least partially artificial pathway.

32. The method of claim 29, wherein:

the artificial pathway includes a section having a maximum outer diameter when measured on a first plane tangential to and on a surface of the bone at the location where the at least partially artificial pathway extends to the bone, of about 1% to about 20% of the wavelength of the vibrations producing the vibrational energy.

33. The method of claim 29, wherein:

the conducting includes attenuating some of the vibrational energy that is otherwise conducted from the vibratory element to the bone.

* * * * *